United States Patent
Gorke et al.

(10) Patent No.: US 12,358,860 B2
(45) Date of Patent: *Jul. 15, 2025

(54) PROCESS FOR GENERATING ACID ANHYDRIDES

(71) Applicant: Cleantech Building Materials PLC, Longdon (GB)

(72) Inventors: Johnathan Gorke, Charlotte, NC (US); Brian Hashiguchi, Naperville, IL (US); Michael Konnick, Aurora, IL (US); Jeffrey Elks, Baton Rouge, LA (US); Jeremy Patt, Erie, CO (US); Juan Gamboa, Brookfield, IL (US)

(73) Assignee: Cleantech Building Materials PLC, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/067,708

(22) Filed: Dec. 17, 2022

(65) Prior Publication Data

US 2023/0120038 A1 Apr. 20, 2023

Related U.S. Application Data

(63) Continuation of application No. 17/314,342, filed on May 7, 2021, now Pat. No. 11,608,306.
(Continued)

(51) Int. Cl.
*C07C 51/56* (2006.01)
*C07C 51/083* (2006.01)
(Continued)

(52) U.S. Cl.
CPC .......... *C07C 51/56* (2013.01); *C07C 51/083* (2013.01); *C07C 67/08* (2013.01); *C07C 67/54* (2013.01); *C07C 67/58* (2013.01)

(58) Field of Classification Search
CPC ......... C07C 67/08; C07C 67/54; C07C 67/58; C07C 51/56; C07C 53/12; C07C 51/83
See application file for complete search history.

(56) References Cited

U.S. PATENT DOCUMENTS 2,116,657 A * 5/1938 Dreyfus .................. C07C 51/56
562/893
2,260,391 A * 10/1941 Maude .................... C07C 51/56
562/894
(Continued)

FOREIGN PATENT DOCUMENTS

CN 1708473 A 12/2005
CN 101466660 A 6/2009
(Continued)

OTHER PUBLICATIONS

Kumar, et al., Aluminum chloride catalyzed one-pot synthesis of 2-aryl substituted benzimidazoles and their antibacterial activity, Indian Journal of Pharmacy and Pharmacology 4(4), pp. 198-202 (Year: 2017).*
(Continued)

*Primary Examiner* — Yate' K Cutliff
(74) *Attorney, Agent, or Firm* — Leydig, Voit & Mayer, Ltd.

(57) ABSTRACT

Provided is a method of producing an anhydride of an organic mono-acid comprising contacting an organic mono-acid and a thermally regenerable anhydride to produce the anhydride of the organic mono-acid, and either a diacid of the regenerable anhydride, a partially hydrolyzed regenerable anhydride, or both. In a particular example, acetic acid and glutaric anhydride can be reacted to form acetic anhydride.

21 Claims, 4 Drawing Sheets

Related U.S. Application Data

(60) Provisional application No. 63/022,075, filed on May 8, 2020.

(51) Int. Cl.
    *C07C 67/08*     (2006.01)
    *C07C 67/54*     (2006.01)
    *C07C 67/58*     (2006.01)

(56) References Cited

U.S. PATENT DOCUMENTS

| | | |
|---|---|---|
| 3,111,548 A | 11/1963 | Altenschöpfer et al. |
| 3,513,180 A * | 5/1970 | Fenton .................. C07C 51/56 562/895 |
| 4,002,677 A | 1/1977 | Naglieri et al. |
| 4,191,695 A * | 3/1980 | Neri .................. C09H 1/04 549/262 |
| 4,195,035 A | 3/1980 | Kleiner et al. |
| 7,473,794 B2 | 1/2009 | Wehner et al. |
| 11,608,306 B2 | 3/2023 | Gorke et al. |
| 2010/0069666 A1 | 3/2010 | Broell |
| 2021/0347722 A1 | 11/2021 | Gorke et al. |

FOREIGN PATENT DOCUMENTS

| | | | |
|---|---|---|---|
| CN | 102675080 A * | 9/2012 | ............ C07C 51/56 |
| CN | 102675080 B | 6/2014 | |
| DE | 408715 C | 1/1925 | |
| GB | 570271 A | 6/1945 | |
| JP | 4164908 B2 * | 3/2000 | ........... C01B 25/234 |
| JP | 2000-229897 A | 8/2000 | |
| WO | 2007/147653 A1 | 12/2007 | |

OTHER PUBLICATIONS

Gu et al., Research progress on azeotropic distillation technology, Advances in Chemical Engineering and Science, vol. 9, pp. 333-342 (Year: 2019).*

Haddadin, M.J., et al., Solvolytic Reactions of Cyclic Anhydrides in Anhydrous Acetic Acid, J. Pharm. Sci. vol. 64, No. 11, pp. 1759-1765 (Year: 1975).*

Besrat et al., "Mammalian Metabolism of Glutaric Acid," *J. Biol. Chem.*, 1969, 244(6), 1461-1467.

Cason, "β-Methylglutaric Anhydride," *Organic Syntheses*, 1958, 38, 52.

Clariant, "Polyphosphoric acid 84%," Nov. 3, 2011. https://web.archive.org/web/20160319003330/https://www.clariant.com/en/Solutions/Products/2014/03/18/16/34/Polyphosphoric-acid-84.

Guo et al., "Research Progress on Azeotropic Distillation Technology," *Advances in Chemical Engineering and Science*, 9: 333-342 (2019).

Haddadin et al., "Solvolytic Reactions of Cyclic Anhydrides in Anhydrous Acetic Acid," *J. Pharm. Sci.*, 1975, 64(11), 1759-1765.

Kumar et al., "Aluminum chloride catalyzed one-pot synthesis of 2-aryl substituted benzimidazoles and their antibacterial activity," *Indian Journal of Pharmacy and Pharmacology*, 4(4): 198-202 (2017).

Wikipedia, "Phosphorus Pentoxide," Dec. 1, 2019. https://en.wikipedia.org/w/index.php?title=Phosphorus_pentoxide&oldid=9286902 29.

International Search Report for PCT/US2021/031252, Aug. 17, 2021.

China National Intellectual Property Administration, First Office Action and Search Report in Chinese Patent Application No. 202180034015.8 (Apr. 24, 2024).

European Patent Office, Extended European Search Report issued in European Patent Application No. 21800935.5 (Jun. 27, 2024).

* cited by examiner $H_6P_4O_{13} + H_2O \longrightarrow H_5P_3O_{10} + H_3PO_4$ (1)
$H_5P_3O_{10} + H_2O \longrightarrow H_4P_2O_7 + H_3PO_4$ (2)
$H_4P_2O_7 + H_2O \longrightarrow 2\ H_3PO_4$ (3)

or (4)

(5)

PROCESS FOR GENERATING ACID ANHYDRIDES

CROSS-REFERENCE TO A RELATED APPLICATION

This patent application is a continuation of U.S. patent application Ser. No. 17/314,342, filed May 7, 2021, which claims the benefit of U.S. Provisional Patent Application No. 63/022,075, filed May 8, 2020, which are incorporated by reference.

BACKGROUND OF THE INVENTION

Anhydrides are useful, reactive species that are often used as water scavengers or acylation agents in chemical processes. Direct condensation of acids to anhydrides is an energetically unfavorable reaction, particularly for mono-acid species, so the synthesis of these anhydrides typically is energy intensive, carried out at elevated temperatures and pressures, and/or is poorly selective in product formation.

Acetic anhydride is produced commercially by three routes: ketene reaction, carbonylation of methyl acetate, and direct oxidation of acetaldehyde. The ketene route is the most widely practiced industrial acetic anhydride process and involves pyrolyzing acetic acid or acetone to ketene at reduced pressure and very high temperature, then reacting the ketene with acetic acid at near ambient temperature in a compressor (see, e.g., U.S. Pat. No. 3,111,548). The carbonylation process involves esterification of acetic acid with methanol to form methyl acetate at moderate temperature. The methyl acetate is then reacted with carbon monoxide at elevated temperature and high pressure (see, e.g., U.S. Pat. No. 4,002,677). Water is also added to the reactor to control the ratio of acetic acid and acetic anhydride. While it is conducted at low temperature and pressure, the direct oxidation of acetaldehyde route suffers from low selectivity (about 80 mol % versus greater than 90 mol % for the other routes) making it economically unattractive. Analogous versions of the above routes are known for producing other anhydrides, although one common technique is to use excess acetic anhydride to produce other desired anhydrides.

Production of acetic anhydride from reacting acetic acid with a cyclic anhydride has been described in the literature (Haddadin et al., *J. Pharm. Sci.*, 1975, 64(11), 1759-1765). However, these experiments rely on having a large excess of acetic acid present as well as a strong acid catalyst (e.g., perchloric acid) to achieve <10% acetic anhydride (relative to acetic acid). As this equilibrium lies heavily on the side of glutaric anhydride, one efficient and practiced industrial method for glutaric anhydride production involves treatment of glutaric acid and its derivatives with a slight excess of acetic anhydride to generate glutaric anhydride quantitatively (Cason, *Org. Synth.*, 1958, 38, 52; and Besrat et al., *J. Biol. Chem.*, 1969, 244(6), 1461-1467). In practice however, this reaction is presumed to be practically irreversible, no processes have described utilization of this reverse reaction to generate acetic anhydride, and no methods utilizing low acetic acid/glutaric anhydride ratios have been described to date. Furthermore, the coupling of this type of non-thermally generable anhydride production reaction with a thermally regenerable anhydride reaction (e.g., glutaric acid to glutaric anhydride and water) to create a continuous process has not been described.

Thus, there remains a need for alternative syntheses for producing anhydrides that work under less harsh conditions while still maintaining a high degree of selectivity.

BRIEF SUMMARY OF THE INVENTION

The invention provides a method of producing an anhydride of an organic mono-acid comprising contacting an organic mono-acid and a thermally regenerable anhydride to produce the anhydride of the organic mono-acid and either a diacid of the regenerable anhydride, a partially hydrolyzed regenerable anhydride, or both a diacid of the regenerable anhydride and a partially hydrolyzed regenerable anhydride.

DETAILED DESCRIPTION OF THE INVENTION

The invention provides an anhydride synthesis that occurs at ambient or near-ambient pressure and moderate temperatures (e.g., about 200° C. or lower). Moreover, the process does not require a catalyst to generate anhydride at high selectivity, although a catalyst can be added. The process can use relatively inexpensive dehydrating agents, including industrial byproducts (e.g., glutaric anhydride) and/or low-cost materials (e.g., polyphosphoric acid). As an added advantage, the inventive process does not require adding a third component (e.g., water) to the system to control the acid/anhydride ratio as needed in the standard carbonylation process. Rather, the residence time and/or relative flow rates of the starting acid and regenerable anhydride can be manipulated to adjust the ratio.

Figure 1:
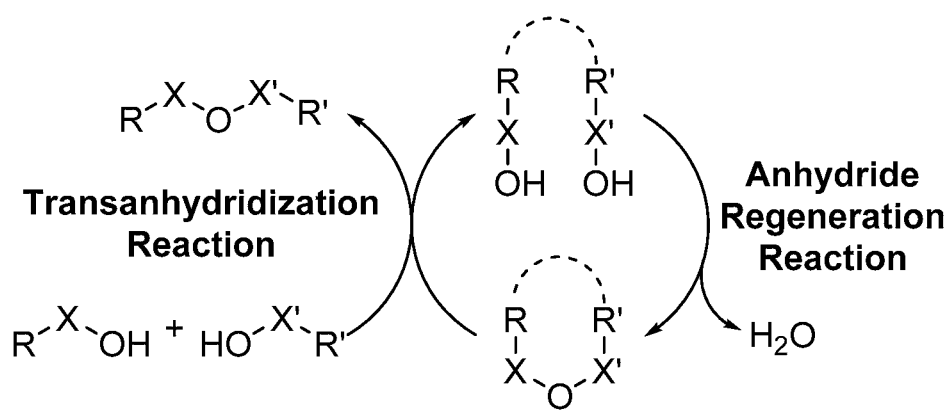
FIG. 1 contains two different generalized schemes illustrating the two-step process of: 1) conversion of an organic mono-acid and a regenerable anhydride to the anhydride or mixed anhydride of the organic mono-acid and the hydrolyzed regenerable anhydride (transanhydridization reaction) and 2) the regeneration of the regenerable anhydride with loss of water (anhydride regeneration reaction).
Figure 1:
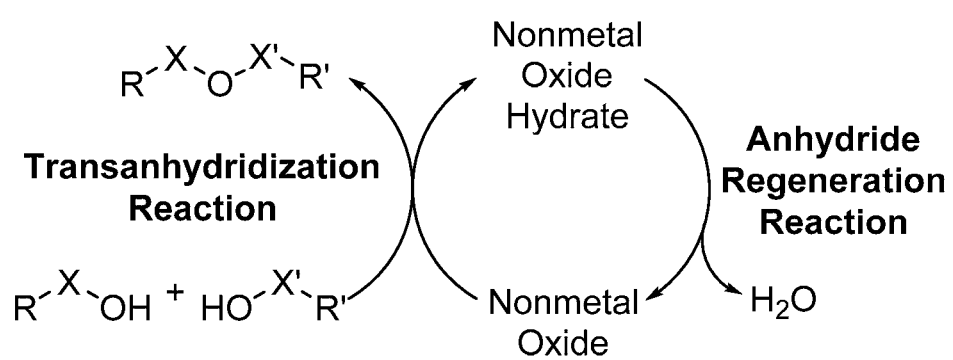
Figure 2:
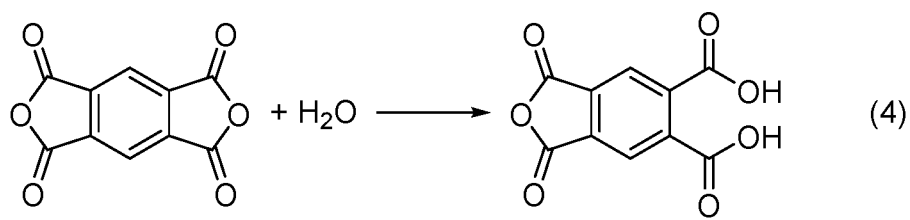
FIG. 2 is a series of reactions showing hydrolysis of an anhydride to form a partially hydrolyzed anhydride using, for example, polyphosphoric acid and pyromellitic anhydride.
Figure 2:
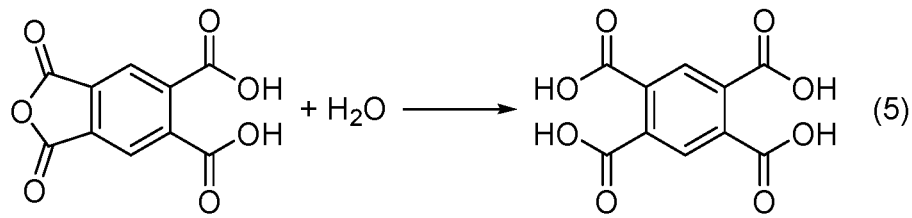

In particular, the invention provides a method of producing an anhydride of an organic mono-acid comprising contacting an organic mono-acid and a thermally regenerable anhydride to produce the anhydride of the organic mono-acid and either a diacid of the thermally regenerable anhydride, a partially hydrolyzed anhydride, or both a diacid of the anhydride and a partially hydrolyzed anhydride. This transanhydridization reaction is illustrated in FIG. 1. Generation of a partially hydrolyzed anhydride is shown in FIG. 2. In general, a stream containing at least one organic mono-acid ("organic mono-acid" or "organic acid") is reacted with a stream containing at least one anhydride that is capable of being regenerated ("thermally regenerable anhydride" or "regenerable anhydride"). The reaction yields a stream containing one or more desired anhydrides and the acid form(s) of the regenerable anhydride(s), as well as unreacted acid and unreacted, regenerable anhydride. The reaction can be run to completion or to partial completion at various ratios of the reactants.

Following the reaction, the residual reactants and products are separated into various streams in one or more steps. For example, the method comprises a separation step comprising forming a first stream comprising the anhydride of the organic mono-acid (desired product) and any unreacted organic mono-acid and forming a second stream comprising the diacid of the regenerable anhydride, partially hydrolyzed anhydride, and/or unreacted anhydride. In some embodiments, residual unreacted regenerable anhydride is extracted from its acid form to drive the regeneration reaction forward.

The separation steps described herein can use any suitable method of physical separation, including distillation (e.g., simple, molecular, evaporative, short path, batch, continuous, flash, steam, vacuum, low temperature, fractional, azeotropic, extractive, or a combination thereof). In some embodiments and depending on the reactants, the separation step is by either fractional distillation, azeotropic distillation, and/or extractive distillation.

In an azeotropic distillation or other distillation with two or more compounds with a close boiling point differential, typically a new component (e.g., entrainer) is added to the azeotrope or otherwise inseparable mixture. The new component serves to form two or more immiscible liquid phases that can be separated. In addition, a third component such as a solid dehydrating agent can be added, e.g., molecular sieves, silica gel, alumina, other thermally regenerable solid drying agents, and combinations thereof.

Azeotropic distillation can be performed as homogenous azeotropic distillation, heterogeneous azeotropic distillation, reactive distillation, and salted distillation. In homogenous azeotropic distillation, an entrainer is added that is miscible with the original mixture. In heterogeneous azeotropic distillation, an entrainer is added that forms a heterogeneous azeotrope with one or more components in the original mixture. In reactive distillation, an entrainer is added that reacts with one or more components in the original mixture. The non-reacting component is produced as a distillate, and the entrainer is recovered from the reverse reaction. Salted distillation is a type of extractive distillation, in which relative volatility is altered by the addition of salt as an entrainer.

In certain embodiments, the unreacted organic mono-acid is separated from the anhydride of the organic mono-acid. If desired, the separated, unreacted organic mono-acid can be recycled for reuse as a starting material. In some instances, a portion of the unreacted organic mono-acid is diverted to a vessel containing the second stream. In such instances, it is believed that the recycled organic mono-acid can act as an entrainer or azeotroping agent to remove water during regeneration of the regenerable anhydride.

The regenerable anhydride is regenerated by removing water from the multi-acid form of the regenerable anhydride. In any of the foregoing embodiments, to regenerate the anhydride the second stream can be optionally heated in the presence or absence of a catalyst and subjected to distillation (e.g., azeotropic distillation). Preferably, the regenerable anhydride is regenerated in a separate step from the reaction that generates the anhydride of the organic mono-acid. In some preferred embodiments, the regenerated anhydride can be recycled for reuse as a starting material.

The reactants and products of the inventive method can be separated and/or concentrated by a number of different unit operations. The reaction and separation steps can be combined or coupled. Similarly, the separation and regeneration steps can be combined or coupled. Unit operations include, for example, distillation, extractive distillation, reactive distillation, extraction, reactive extraction, mixing-settling, pervaporation, membrane separation, evaporation, condensation, flashing, fractionation, electrotreatment, flotation, phase separation, coalescence, hydrocycloning, decanting, parametric pumping, sublimation, ion exchange, adsorption, absorption, and/or crystallization.

In the method, the anhydride starting material is any suitable regenerable anhydride. In some instances, the regenerable anhydride is cyclic or can form a cyclic structure. It has been observed that an anhydride with a cyclic structure or that can form a cyclic structure can be more easily thermally regenerated. In some embodiments, the thermally regenerable anhydride is selected from a carboxylic acid anhydride, a sulfonic acid anhydride, a phosphinic acid anhydride, a phosphonic acid anhydride, a phosphoric acid anhydride, and a mixed anhydride. In some embodiments, the mixed anhydride contains a combination of different acid moieties. In some embodiments, the mixed anhydride has different backbone structures (e.g., a mixed anhydride created from the condensation of the organic mono-acid in the feed and another acidic moiety). Preferably, at least a portion of the structure of the mixed anhydride is in cyclic form or capable of forming a cyclic structure.

In general, the regenerable carboxylic acid anhydride can have a cyclic structure of the formula $R^1$—C(O)—O—C(O)—$R^2$, in which $R^1$ and $R^2$ are linked together to form an alkylene with 1 or 2 optional double bonds, arylene, or a mixed alkylene/arylene group. The mixed alkylene/arylene group can in some instances form dianhydride or trianhydride. The alkylene with 1 or 2 optional double bonds, arylene, and mixed alkylene/arylene group is optionally substituted with one or more substituents (e.g., 1, 2, 3, 4, 5, 6, etc.) selected from alkyl (including alkylene), halo, alkoxy, trialkylsiloxy, nitro, aryl, and carboxy-substituted phenyl. Examples of the carboxylic acid anhydride include, e.g., tetrafluorosuccinic anhydride, maleic anhydride, itaconic anhydride, succinic anhydride, glutaric anhydride, 2,7-oxepanedione (adipic anhydride), azelaic anhydride, suberic anhydride, sebacic anhydride, 3-methylglutaric anhydride, methylsuccinic anhydride, 3-(t-butyldimethylsilyloxy)glutaric anhydride, 1,2-cyclohexanedicarboxylic anhydride, 1,3-cyclohexanedicarboxylic anhydride, camphoric anhydride, homophthalic anhydride, phthalic anhydride, isophthalic anhydride, trimellitic anhydride, pyromellitic dianhydride, mellitic trianhydride, and 3- or 4-fluorophthalic anhydride.

In general, the regenerable sulfonic acid anhydride has the formula $R^3$—S(O)$_2$—O—S(O)$_2$—$R^4$, in which $R^3$ and $R^4$ are the same or different and each is a $C_{1-12}$ alkyl group or aryl group (e.g., phenyl) or $R^3$ and $R^4$ are linked together to form an alkylene, arylene, or mixed alkylene/arylene group. Each $C_{1-12}$ alkyl, aryl, alkylene, arylene, and mixed alkylene/arylene group is optionally substituted with one or more substituents (e.g., 1, 2, 3, 4, or 5) selected from alkyl, halo, alkoxy, trialkylsiloxy, nitro, and aryl. Examples of the sulfonic acid anhydride include, e.g., methanesulfonic anhydride, 1,2-ethane disulfonic anhydride, nonafluorobutane-sulfonic anhydride, and p-toluenesulfonic anhydride.

A regenerable phosphinic acid anhydride has the formula $R^5$—P(O)($R^6$)—O—P(O)($R^7$)—$R^8$ in which $R^5$, $R^6$, $R^7$, and $R^8$ are the same or different and each is H, a $C_{1-12}$ alkyl group, or aryl group (e.g., phenyl) or $R^5$ and $R^8$ are linked together to form an alkylene, arylene, or mixed alkylene/arylene group. Each $C_{1-12}$ alkyl, aryl, alkylene, arylene, and mixed alkylene/arylene group is optionally substituted with one or more substituents (e.g., 1, 2, 3, 4, or 5) selected from alkyl, halo, alkoxy, trialkylsiloxy, nitro, and aryl. Examples of the phosphinic acid anhydride include, e.g., propane-1, 3-bis(methylphosphinic acid) anhydride, butane-1,4-bis (methylphosphinic acid) anhydride, hexane-1,6-bis(methylphosphinic acid) anhydride and decane-(1,10-bismethylphosphinic acid) anhydride.

A regenerable phosphonic acid anhydride has the formula $R^9$—P(O)(OH)—O—P(O)(OH)—$R^{10}$, $R^9$—P(O)(OH)—[O—P(O)($R^{10}$)]$_n$—O—P(O)(OH)—$R^{11}$, or

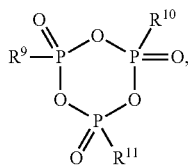

in which $R^9$, $R^{10}$, and $R^{11}$ are the same or different and each is a $C_{1-12}$ alkyl group or aryl group (e.g., phenyl) or $R^9$ and $R^{10}$ are linked together to form an alkylene, arylene, or mixed alkylene/arylene group. Each $C_{1-12}$ alkyl, aryl, alkylene, arylene, and mixed alkylene/arylene group is optionally substituted with one or more substituents (e.g., 1, 2, 3, 4, or 5) selected from alkyl, halo, alkoxy, trialkylsiloxy, nitro, and aryl. Examples of the phosphonic acid anhydride include, e.g., propane-phosphonic acid anhydride, butane-phosphonic acid anhydride, hexane-phosphonic acid anhydride, octane-phosphonic acid anhydride, decane-phosphonic acid anhydride, methane-pyrophosphonic acid anhydride, and propane-pyrophosphonic acid anhydride.

A regenerable phosphoric acid anhydride includes, for example, phosphorus pentoxide, pyrophosphoric acid, trimetaphosphoric acid, polyphosphates, cyclic polyphosphates, and polyphosphoric acid.

In some embodiments, the regenerable anhydride forms a polymeric structure. Typically, polymeric structures form with alkyene chains longer than 5 carbons (e.g., C6, C7, C8, C9, C10, etc.). It is believed that a polymeric structure forms when the terminus of one molecule bonds to the terminus of a second molecule and so on. A diacid that forms a polyanhydride can be of the formula $HO_2C$—$(CH_2)_m$—C(O)—O—C(O)—$(CH_2)_n$—$CO_2H$, in which m and n are the same or different and each is an integer from 6 to 12 (i.e., 6, 7, 8, 9, 10, 11, or 12). In some embodiments, the polyanhydride can be of the formula:

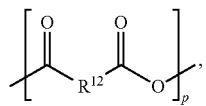

in which $R^{12}$ is $C_{6-12}$ alkylene that optionally contains one or more double bonds, arylene, or a mixture thereof. The alkylene and arylene can be substituted as described herein. The subscript "p" is the number of repeat units and is an integer of at least 2 (e.g., 5 or more, 10 or more, 15 or more, etc.). Examples of the diacid anhydride that can form a polyanhydride include, e.g., adipic anhydride, azelaic anhydride, suberic anhydride, sebacic anhydride, decane anhydride, dodecanedioic anhydride, 1,6-bis(p-carboxyphenoxy) hexane anhydride, 1,3-bis(p-carboxyphenoxy)propane anhydride, p-carboxyphenoxymethane anhydride, p-carboxyphenoxypropane anhydride, p-carboxyphenoxyvaleric anhydride, p-carboxyphenoxyacetic anhydride, p-carboxyphenoxy octanoic anhydride, phenylenedipropionic anhydride, and combinations thereof. The polymeric anhydride can also be mixed in that two different acids are condensed, such as sebacid acid copolymerized with 1,3-bis(p-carboxyphenoxy)propane or 1,6-bis(p-carboxyphenoxy)hexane.

In certain instances, the regenerable anhydride is a mixture of anhydrides that are in cyclic form, capable of forming a cyclic structure, and/or polymeric form.

The regenerable anhydride can also be a mixed anhydride, which includes different organic groups of a single type of anhydride (e.g., benzoic acid-trifluoroacetic acid anhydride) and an anhydride of both a carboxylic acid and a sulfonic acid (e.g., ortho/meta/para-sulfobenzoic anhydride, including mixtures thereof), a carboxylic acid and a phosphoric acid, or a sulfonic acid and a phosphoric acid. In some instances, a mixed anhydride is created from the condensation of the organic mono-acid and another acidic moiety present in the reaction.

In preferred embodiments, the regenerable anhydride is succinic anhydride, glutaric anhydride, nitrophthalic anhydride, homophthalic anhydride, 1,2-ethane disulfonic acid anhydride, polyphosphoric acid, pyromellitic anhydride, propanephosphonic anhydride, ortho-sulfobenzoic anhydride, mixed benzoic acid-trifluoroacetic acid anhydride, or any combination thereof. More preferably, the anhydride is glutaric anhydride.

The regenerable anhydride can be added to the reaction in any suitable manner.

The organic mono-acid is a carboxylic acid, a sulfonic acid, a sulfinic acid, a phosphonic acid, or a phosphinic acid. In general, the carboxylic acid is of the formula R—C(O) OH; the sulfonic acid is of the formula R—S(O)$_2$OH; the sulfinic acid is of the formula R—S(O)OH; the phosphonic acid is of the formula R—P(O)(OH)$_2$; and the phosphinic acid is of the formula R—P(R')(O)OH. In any of the foregoing formulas, R is $C_{1-18}$ alkyl or aryl. R' is H, $C_{1-18}$ alkyl, or aryl. The $C_{1-18}$ alkyl and aryl groups for R and R' can be optionally substituted with one or more substituents (e.g., 1, 2, 3, 4, 5, 6, etc.) selected from alkyl, halo, alkoxy, trialkylsiloxy, nitro, and aryl.

In some instances, the organic mono-acid is a $C_{1-18}$ monocarboxylic acid, a halo-substituted $C_{1-18}$ monocarboxylic acid (e.g., chloroacetic acid or trifluoroacetic acid), an aryl-containing acid (e.g., benzoic acid or cinnamic acid), methanesulfonic acid, or a combination thereof.

In some instances, the organic mono-acid is a $C_{1-18}$ monocarboxylic acid such as, e.g., formic acid, acetic acid, propionic acid, butanoic acid (butyric acid), isobutyric acid, pentanoic acid (valeric acid), hexanoic acid (caproic acid), heptanoic acid, octanoic acid (caprylic acid), nonanoic acid (pelargonic acid), decanoic acid (capric acid), undecanoic acid (undecylic acid), dodecanoic acid (lauric acid), tridecanoic acid (tridecylic acid), tetradecanoic acid (myristic acid), pentadecanoic acid (pentadecylic acid), hexadecanoic acid (palmitic acid), heptadecanoic acid (margaric acid), octadecanoic acid (stearic acid), or a combination thereof. In a preferred embodiment, the organic mono-acid is acetic acid.

If desired, the organic mono-acid can be added in the form of a salt. While not wishing to be bound by any theory, it is believed that a salt facilitates generation of non-volatile mixed anhydride intermediates that are more kinetically favorable for forming the desired anhydride product from the organic mono-acid (e.g., monocarboxylic acid) than the anhydride (e.g., cyclic anhydride) alone. The organic mono-acid can be, for example, a salt of an alkali metal (e.g., Group 1 cations, such as lithium, sodium, or potassium), an alkaline earth metal (e.g., Group 2 cations, such as calcium, magnesium, and barium), a transition metal (e.g., Group 3-12 cations, such as Fe(II), Zn(II), Cu(I), Cu(II), Cr(II), Al(III), Mn(II), or Ni(II)), or ammonium. In any of the foregoing formulas of the organic mono-acid, one or more hydrogens can be replaced with a cation ($X^+$), such as R—C(O)—$O^-X^+$. Examples of a salt of an organic mono-acid include, e.g., lithium acetate and potassium isobutyrate.

The organic mono-acid can be present in the reactor and/or added to the reaction in a single stage or over multiple stages (e.g., 2 or more stages, 3 or more stages, 4 or more stages, 5 or more stages, 6 or more, etc.). Additionally, the organic mono-acid can be added in an amount that is sub-stoichiometric to, stoichiometric to, or in excess of the regenerable anhydride. In certain embodiments, the organic mono-acid is present in the reactor in an amount that is in excess of the regenerable anhydride. In such scenarios, the ratio of organic mono-acid to regenerable anhydride ranges from 1:1 to 10:1 or is 1:1 or more (e.g., 2:1 or more, 3:1 or more, 4:1 or more, 5:1 or more, 6:1 or more, 7:1 or more, 8:1 or more, or 9:1 or more) and/or 10:1 or less (e.g., 9:1 or less, 8:1 or less, 7:1 or less, 6:1 or less, 5:1 or less, 4:1 or less, 3:1 or less, or 2:1 or less). Any two of the foregoing endpoints can be used to define a close-ended range, or a single endpoint can be used to define an open-ended range.

In any of the embodiments above, the term "alkyl" implies a straight-chain or branched alkyl substituent containing from, for example, from about 1 to about 18 carbon atoms, e.g., from about 1 to about 14 carbon atoms, from about 1 to about 12 carbon atoms, from about 1 to about 10 carbon atoms, from about 1 to about 8 carbon atoms, from about 1 to about 6 carbon atoms, or from about 1 to about 4 carbon atoms. Examples of alkyl group include methyl, ethyl, n-propyl, isopropyl, n-butyl, sec-butyl, isobutyl, tert-butyl, n-pentyl, isopentyl, n-hexyl, n-heptyl, n-octyl, n-nonyl, n-decyl, n-dodecyl, and the like. The alkyl can be substituted or unsubstituted, as described herein.

The term "alkylene" refers to a divalent alkyl group, such as methylenyl (—$CH_2$—), ethylene (—$CH_2CH_2$—), propylene (—$CH_2CH_2CH_2$—), etc., in which the alkyl group is as described above. The alkylene can optionally include 1 or 2 double bonds, such as (—CH=CH—), (—CH=CHCH$_2$—), or (—$CH_2$CH=CH—). Preferably, the alkylene contains from about 1 to about 6 carbon atoms, from about 1 to about 4 carbon atoms, or from about 1 to about 3 carbon atoms. The alkylene can be substituted as described herein.

In any of the embodiments above, the term "aryl" refers to a mono, bi, or tricyclic carbocyclic ring system having one, two, or three aromatic rings, for example, phenyl, naphthyl, anthracenyl, or biphenyl. The term "aryl" refers to an unsubstituted or substituted aromatic carbocyclic moiety, as commonly understood in the art, and includes monocyclic and polycyclic aromatics such as, for example, phenyl, biphenyl, naphthyl, anthracenyl, pyrenyl, and the like. Preferably, the aryl is phenyl. An aryl moiety generally contains from, for example, 6 to 30 carbon atoms, from 6 to 18 carbon atoms, from 6 to 14 carbon atoms, or from 6 to 10 carbon atoms. It is understood that the term aryl includes carbocyclic moieties that are planar and comprise $4n+2$ π electrons, according to Hückel's Rule, wherein n=1, 2, or 3. The aryl can be substituted or unsubstituted, as described herein.

The term "arylene" refers to a divalent aryl group, such as divalent phenylene, etc., in which the aryl group is as described above. The arylene can be substituted as described herein.

In any of the embodiments above, the term "halo" refers to a halogen moiety selected from fluoro, chloro, bromo, and iodo.

In any of the embodiments above, the term "alkoxy" embrace a linear or branched alkyl group that is attached to a divalent oxygen. The alkyl group is the same as described herein.

The term "at least one" means 1 or more, 2 or more, 3 or more, or 4 or more, including 1, 2, 3, 4, etc.

In any of the foregoing embodiments, the method can further comprise a suitable solvent. One purpose of a solvent may be to increase the rate of anhydride generation of the reaction by manipulating the dielectric constant and/or solvation properties of the mixture. Without wishing to be bound by theory, it is believed that running the reaction in a high dielectric solvent, such as sulfolane or dimethylsulfoxide (DMSO), could allow for more efficient reactions with organic mono-acids, such as polyphosphoric acid and low dielectric carboxylic acids. Another purpose of the solvent may be to act as an entrainer or azeotroping agent to facilitate the separation of compounds in the system, particularly the product from the starting material. A temperature- or pressure-swing distillation system can be used to facilitate further separation of either bottoms, distillate, or both. The solvent can be, for example, can be protic or aprotic and preferably has a dielectric constant ($\varepsilon$) is that is 15 or more (e.g., $\varepsilon$ is 20 or more, 25 or more, 30 or more, 35 or more, 40 or more, etc.). The higher the dielectric constant, the higher the polarity of the solvent. Examples of suitable solvents include acetone, acetonitrile, dimethylacetamide, N,N-dimethylformamide (DMF), formamide, hexamethylphosphoramide, dimethylsulfoxide (DMSO), sulfolane, methanol, ethanol, ispropanol, nitrobenzene, nitromethane, cyclohexanone, methyl ethyl ketone, methyl cyclohexane, toluene, m-xylene, o-xylene, p-xylene, and any combination thereof. A preferred solvent comprises DMSO, sulfolane, or a combination thereof. In some embodiments, a solvent is not used.

While typically not necessary, one or more catalysts can be used. In some embodiments of the inventive method, a catalyst can be used to facilitate the regeneration of the anhydride (e.g., cyclic anhydride), increase the rate of product generation, or both. A suitable catalyst can be homogeneous, insoluble but mobile (e.g., a slurry), or heterogeneous. Examples of catalysts include perchloric acid, magnesium chloride, an ion exchange resin (e.g., a macro reticular (macroporous) polystyrene based ion exchange resin with strongly acidic sulfonic groups, such as AMBERLYST™), a perfluorinated resin (e.g., a sulfonated tetrafluoroethylene-based fluoropolymer-copolymer, such as NAFION™), and a combination thereof.

The transanhydridization reaction (FIG. 2) can be run at any suitable temperature. In general, the transanhydridization reaction temperature is moderate, such as a 200° C. or below, including 180° C. or below, 160° C. or below, 150° C. or below, 145° C. or below, 140° C. or below, 135° C. or below, 130° C. or below, 125° C. or below, 120° C. or below, 115° C. or below, 110° C. or below, 105° C. or below, 100° C. or below, 95° C. or below, 90° C. or below, 85° C. or below, 80° C. or below, 75° C. or below, 70° C. or below, 65° C. or below, 60° C. or below, 55° C. or below, or 50° C. or below. Typically, the transanhydridization reaction temperature is performed at 45° C. or more (e.g., 50° C. or more, 60° C. or more, 70° C. or more, 80° C. or more, 90° C. or more, 100° C. or more, 110° C. or more, 120° C. or more, 130° C. or more, or 140° C. or more). Any two of the foregoing endpoints can be used to define a close-ended range, or a single endpoint can be used to define an open-ended range. In some preferred embodiments, the reaction temperature is about 170° C. or below, more preferably 150° C. or below, 120° C. or below, 115° C. or below, 110° C. or below, or 80° C. or below.

The transanhydridization reaction can be run under any suitable pressure and typically is run at ambient pressure (e.g., atmospheric pressure at 1 atm) or near-ambient pressure (e.g., 1 atm±10%, 1 atm±5%, 1 atm±2%, or 1 atm±1%). In some embodiments, the transanhydridization reaction is run under slight pressure, such as 15 atm or less (e.g., 10 atm or less, 8 atm or less, 6 atm or less, 5 atm or less, 4 atm or less, 3 atm or less, or 2 atm or less). In such embodiments, the reaction pressure typically will be at 1 atm or more (e.g., 2 atm or more, 3 atm or more, 4 atm or more, 5 atm or more, 6 atm or more, 7 atm or more, 8 atm or more, 9 atm or more, 10 atm or more, or 12 atm or more). For the separation step (e.g., the pressure in a stripping column), the pressure typically is lower to help prevent the reverse reaction from proceeding, such as 0.05 atm or more (e.g., 0.1 atm or more, 0.2 atm or more, 0.5 atm or more, 0.8 atm or more, 1 atm or more and/or 5 atm or less, 2 atm or less, 1 atm or less, 0.8 atm or less, 0.5 atm or less, 0.2 atm or less, or 0.1 atm or less). Any two of the foregoing endpoints can be used to define a close-ended range, or a single endpoint can be used to define an open-ended range.

The transanhydridization reaction be can run for any suitable length of time. The reaction time can be 0.01 hours or more (e.g., 0.05 hours or more, 0.1 hours or more, 0.15 hours or more, 0.02 hours or more, 0.25 hours or more 0.5 hours or more, 0.75 hours or more, 1 hour or more, 1.5 hours or more, 2 hours or more, 3 hours or more, 4 hours or more, or 5 hours or more). Typically the reaction run will be complete in 4 days or less (e.g., 3.5 days or less, 3 days or less, 2.5 days or less, 2 days or less, 1 day or less, 20 hours or less, 15 hours or less, 10 hours or less, 8 hours or less, 6 hours or less, 5 hours or less, 4 hours or less, 3 hours or less, 2 hours or less, or 1 hour or less). Any two of the foregoing endpoints can be used to define a close-ended range, or a single endpoint can be used to define an open-ended range.

The anhydride regeneration reaction (FIG. 2) can be run at any suitable temperature that regenerates the anhydride (e.g., 350° C. or below, 325° C. or below, 300° C. or below, 275° C. or below, 250° C. or below, 225° C. or below, 200° C. or below, 175° C. or below, 150° C. or below, 125° C. or below, 100° C. or below, 90° C. or below, 85° C. or below, 80° C. or below, 75° C. or below, 70° C. or below, 65° C. or below, 60° C. or below, 55° C. or below, or 50° C. or below). Typically, the anhydride regeneration reaction temperature is performed at 30° C. or more (e.g., 40° C. or more, 50° C. or more, 60° C. or more, 70° C. or more, 75° C. or more, 80° C. or more, 85° C. or more, 90° C. or more, 100° C. or more, 110° C. or more, 115° C. or more, 125° C. or more, 130° C. or more, 135° C. or more, 140° C. or more, 145° C. or more, 150° C. or more, 175° C. or more, or 200° C. or more). Any two of the foregoing endpoints can be used to define a close-ended range, or a single endpoint can be used to define an open-ended range.

The anhydride regeneration reaction can be run under any suitable pressure and typically is run at atmospheric pressure (about 1 atm) or reduced pressure.

The method has a high selectivity in that minimal byproducts are detected beyond the expected products. For example, the term "high selectivity" means that 85 mol % or more (e.g. 87 mol % or more, 89 mol % or more, 90 mol % or more, 92 mol % or more, 94 mol % or more, 95 mol % or more, 96 mol % or more, 97 mol % or more, 98 mol % or more, or 99 mol % or more) in any conversion observed to form the desired product(s).

In a preferred example of the inventive method, the anhydride is glutaric anhydride, the organic mono-acid is acetic acid, and the anhydride of the monocarboxylic acid is acetic anhydride.

The inventive method can be used to generate anhydrides for use in a subsequent processing step on-site (e.g., cellulose acetate manufacturing) or to generate anhydrides in a solvent for shipment. The process can be collocated with other processes, such as utilizing a glutaric acid byproduct steam of adipic acid manufacturing to generate a more valuable acetic anhydride product stream. The process can be tightly integrated with other processes. For example, in the production of cellulose acetate, the acetic acid byproduct stream could be converted to acetic anhydride raw material, with consideration for heat integration of the unit operations.

In any of the methods described herein, the intrinsic capital intensity of the process in 2020 USD is less than $5,000 (e.g., less than $4,500, less than $4,000, less than $3,500, less than $3,000, less than $2,500, less than $2,000, less than $1,500, or less than $1,000) per ton of installed annual capacity. In some embodiments, the intrinsic capital intensity of the process in 2020 USD is $1,000 or more (e.g., $1,000 or more, $1,500 or more, $2,000 or more, $2,500 or more, $3,000 or more, $3,500 or more, $4,000 or more, or $4,500 or more) per ton of installed annual capacity. Any two of the foregoing endpoints can be used to define a close-ended range, or a single endpoint can be used to define an open-ended range. The installed annual capacity is for a plant size with a capacity of less than 36 thousand metric tons per year (kmta) (e.g., less than 34 kmta, less than 30 kmta, less than 30 kmta, less than 28 kmta, less than 25 kmta, less than 22 kmta, less than 20 kmta, less than 18 kmta, less than 16 kmta, less than 15 kmta, less than 14 kmta, less than 12 kmta, less than 10 kmta, less than 8 kmta, less than 6 kmta, or less than 5 kmta).

In any of the methods described herein, the intrinsic capital intensity of the overall process is more than 5% lower than the intrinsic capital intensity of a ketene-based acetic acid to acetic anhydride process at the same plant size. For example, the intrinsic capital intensity of the overall process preferably is more than 10% lower (e.g., more than 15% lower, more than 20% lower, more than 25% lower, more than 30% lower, more than 35% lower, more than 40% lower) than the intrinsic capital intensity of a ketene-based acetic acid to acetic anhydride process at the same plant size. In any of these embodiments, the plant size is less than 50 kmta capacity (e.g., less than 45 kmta capacity, less than 40 kmta capacity, less than 35 kmta capacity, less than 30 kmta capacity, less than 25 kmta capacity, less than 20 kmta capacity, less than 15 kmta capacity, less than 10 kmta capacity, or less than 5 kmta capacity).

In any of the methods described herein, the intrinsic capital intensity of the ISBL (inside battery limits) equipment of the overall process is more than 5% lower than the intrinsic capital intensity of the ISBL equipment of a ketene-based acetic acid to acetic anhydride process at the same plant size. For example, the intrinsic capital intensity of the ISBL equipment of the overall process preferably is more than 10% lower (e.g., more than 15% lower, more than 20% lower, more than 25% lower, more than 30% lower, more than 35% lower, more than 40% lower) than the intrinsic capital intensity of the ISBL equipment of a ketene-based acetic acid to acetic anhydride process at the same plant size. In any of these embodiments, the plant size is less than 50 kmta capacity (e.g., less than 45 kmta capacity, less than 40 kmta capacity, less than 35 kmta capacity, less than 30 kmta capacity, less than 25 kmta capacity, less than 20 kmta capacity, less than 15 kmta capacity, less than 10 kmta capacity, or less than 5 kmta capacity).

In any of the methods described herein, the intrinsic capital intensity of the ISBL (inside battery limits) and OSBL (outside battery limits) equipment of the overall process is more than 5% lower than the intrinsic capital intensity of the ISBL and OSBL equipment of a ketene-based acetic acid to acetic anhydride process at the same plant size. For example, the intrinsic capital intensity of the ISBL and OSBL equipment of the overall process preferably is more than 10% lower (e.g., more than 15% lower, more than 20% lower, more than 25% lower, more than 30% lower, more than 35% lower, more than 40% lower) than the intrinsic capital intensity of the ISBL and OSBL equipment of a ketene-based acetic acid to acetic anhydride process at the same plant size. In any of these embodiments, the plant size is less than 50 kmta capacity (e.g., less than 45 kmta capacity, less than 40 kmta capacity, less than 35 kmta capacity, less than 30 kmta capacity, less than 25 kmta capacity, less than 20 kmta capacity, less than 15 kmta capacity, less than 10 kmta capacity, or less than 5 kmta capacity).

As used herein, the term "intrinsic capital intensity" refers to the capital cost in dollars, divided by installed annual capacity of a chemical plant performing a specific process or chemical transformation. The intrinsic capital intensity for a process can be defined as that of the ISBL (inside battery limits) equipment or the ISBL plus OSBL (outside battery limits) equipment (either on an installed cost basis), or the entire plant project cost.

The invention is further illustrated by the following aspects.

Aspect (1) A method of producing an anhydride of an organic mono-acid comprising contacting an organic mono-acid and a thermally regenerable anhydride to produce the anhydride of the organic mono-acid and a diacid of the regenerable anhydride or a partially hydrolyzed anhydride.

Aspect (2) The method of aspect (1), wherein the anhydride of the organic mono-acid and the diacid of the regenerable anhydride or partially hydrolyzed anhydride are separated.

Aspect (3) The method of aspect (2), wherein the separation step comprises forming a first stream comprising the anhydride of the organic mono-acid and unreacted organic mono-acid and a second stream comprising the diacid of the regenerable anhydride or partially hydrolyzed anhydride and unreacted anhydride.

Aspect (4) The method of anyone of aspects (1)-(3), wherein the separation step is by distillation.

Aspect (5) The method of aspect (3) or (4), wherein the unreacted organic mono-acid is separated from the anhydride of the organic mono-acid.

Aspect (6) The method of aspect (5), wherein the separated, unreacted organic mono-acid is recycled.

Aspect (7) The method of any one of aspect (3)-(6), wherein the second stream is heated to regenerate the regenerable anhydride.

Aspect (8) The method of aspect (7), wherein azeotropic distillation is used to regenerate the regenerable anhydride.

Aspect (9) The method of aspect (7) or aspect (8), wherein the regenerable anhydride is recycled.

Aspect (10) The method of any one of aspects (1)-(9), wherein the regenerable anhydride is cyclic or can form a cyclic structure.

Aspect (11) The method of any one of aspects (1)-(10), wherein the regenerable anhydride is selected from a carboxylic acid anhydride, a sulfonic acid anhydride, a phosphinic acid anhydride, a phosphonic acid anhydride, and a mixed anhydride containing a combination of different acid moieties or different backbone structures.

Aspect (12) The method of any one of aspects (1)-(11), wherein the regenerable anhydride is selected from succinic anhydride, glutaric anhydride, nitrophthalic anhydride, homophthalic anhydride, 1,2-ethane disulfonic acid, polyphosphoric acid, ortho-sulfobenzoic anhydride, and mixed benzoic acid-trifluoroacetic acid anhydride.

Aspect (13) The method of any one of aspects (1)-(12), wherein the regenerable anhydride is glutaric anhydride.

Aspect (14) The method of any one of aspect (1)-(13), wherein the organic mono-acid is a carboxylic acid, a sulfonic acid, a sulfinic acid, a phosphonic acid, or a phosphinic acid.

Aspect (15) The method of aspect (14), wherein the carboxylic acid is a $C_{1-12}$ monocarboxylic acid.

Aspect (16) The method of aspect (15), wherein the $C_{1-12}$ monocarboxylic acid is selected from formic acid, acetic acid, propionic acid, butanoic acid (butyric acid), isobutyric acid, pentanoic acid (valeric acid), hexanoic acid (caproic acid), heptanoic acid, octanoic acid (caprylic acid), decanoic acid (capric acid), and dodecanoic acid.

Aspect (17) The method of any one of aspects (1)-(16), wherein the organic mono-acid is acetic acid.

Aspect (18) The method of any one of aspects (1)-(17), wherein the anhydride of the monocarboxylic acid is acetic anhydride.

Aspect (19) The method of any one of aspects (1)-(18), wherein the organic mono-acid is added in excess of the anhydride.

Aspect (20) The method of any one of aspects (1)-(19), wherein the organic mono-acid is added over multiple stages.

Aspect (21) The method of any one of aspects (1)-(20) further comprising adding a salt of the organic mono-acid.

Aspect (22) The method of any one of aspects (1)-(21) further comprising a solvent.

Aspect (23) The method of any one of aspects (1)-(22) further comprising a catalyst.

Aspect (24) The method of any one of aspects (3)-(23), wherein a portion of the monocarboxylic acid is diverted to a vessel containing the second stream.

The following examples further illustrate the invention but, of course, should not be construed as in any way limiting its scope.

Example 1

This example demonstrates a general method of producing an anhydride of an organic mono-acid by reacting an organic mono-acid and a regenerable anhydride.

A low-boiling monocarboxylic acid (such as acetic acid, propionic acid, or isobutyric acid) is fed to a reactor and reacted with a higher-boiling regenerable cyclic anhydride (such as succinic anhydride, glutaric anhydride, 1,2-ethane-disulfonic acid anhydride, or ortho-sulfobenzoic anhydride) to generate the anhydride of the monocarboxylic acid and the diacid form of the regenerable cyclic anhydride.

Figure 3:
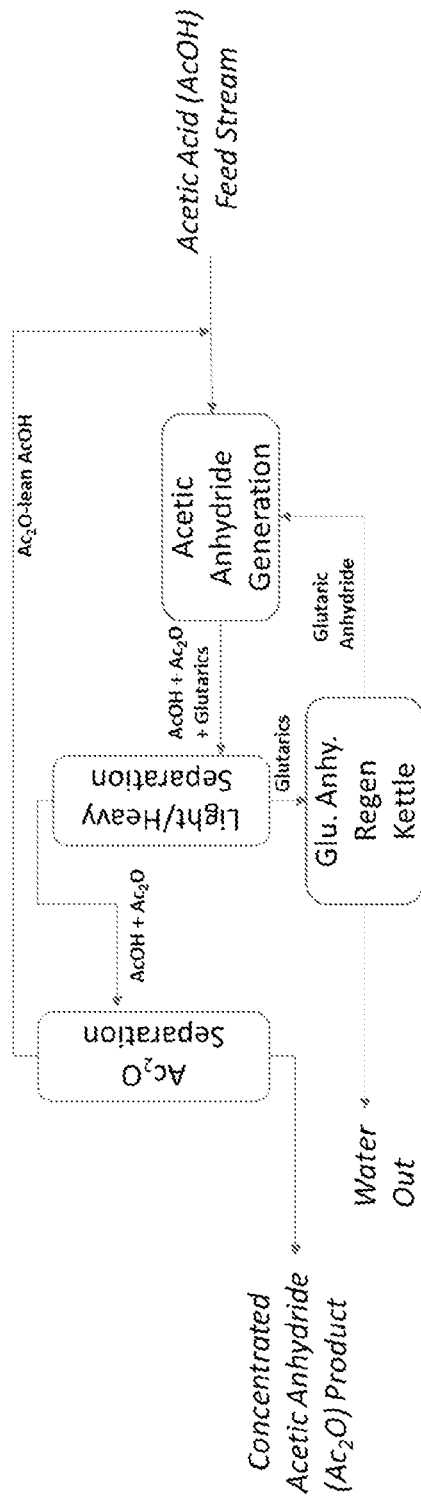
FIG. 3 is a scheme illustrating an acetic acid feed (AcOH) feed and a glutaric anhydride feed to generate acetic anhydride ($Ac_2O$).
Figure 4:
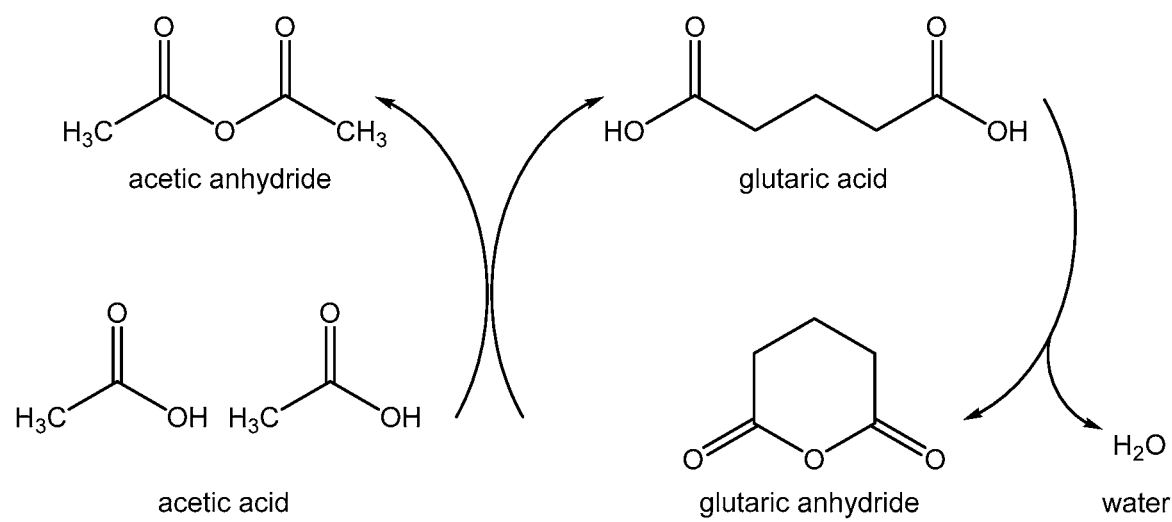
FIG. 4 is a reaction scheme illustrating acetic acid (organic mono-acid) reacting with glutaric anhydride (regenerable anhydride) to form acetic anhydride (anhydride of the organic mono-acid) and glutaric acid (diacid of the anhydride), which is subsequently dehydrated to reform glutaric anhydride (regenerable anhydride).

The mixture of products and starting material is separated in a series of flash stages or distillations to yield a first stream principally comprised of the generated anhydride and residual monocarboxylic acid and a second stream principally comprised of the residual regenerable cyclic anhydride and the generated diacid of the regenerable cyclic anhydride. The stream containing the anhydride product is then further concentrated in the anhydride product through partial condensation, flash, or distillation, and most of the residual monocarboxylic acid is recycled to the initial reactor. The stream containing residual regenerable cyclic anhydride is regenerated thermally, generated water is removed, and the regenerable cyclic anhydride is recycled to the reactor. FIG. 3 is a scheme illustrating an acetic acid feed (AcOH) feed and a glutaric anhydride feed to generate acetic anhydride ($Ac_2O$). FIG. 4 shows the reaction scheme for this process. Acetic acid (organic mono-acid) is reacted with glutaric anhydride (regenerable anhydride) to form acetic anhydride (anhydride of the organic mono-acid) and glutaric acid (diacid of the regenerable anhydride). The glutaric acid is dehydrated to regenerate the glutaric anhydride (regenerable anhydride).

Example 2

This example demonstrates a method of producing various anhydrides using a regenerable anhydride and an organic mono-acid in an embodiment of the invention.

Following the procedure set forth in Example 1, solutions of regenerable anhydride in organic mono-acid were heated at either 50° C. or 100° C. for the indicated time in a batch reactor. No solvents or catalysts were used. The products were analyzed by nuclear magnetic resonance (NMR) spectra. No byproducts were detected by NMR, suggesting very high selectivity. The results of these experiments are set forth in Table 1.

TABLE 1

| Organic mono-acid (concentration (M)) | Regenerable Anhydride (concentration (M)) | Temperature (° C.) | Time (hr) | Acid Conversion (mol %) |
|---|---|---|---|---|
| Acetic Acid (16.0) | Glutaric Anhydride (1.0) | 50 | 0.5 | 2.8 |
| Acetic Acid (14.4) | Glutaric Anhydride (2.0) | 50 | 0.5 | 4.3 |
| Acetic Acid (11.3) | Glutaric Anhydride (4.0) | 50 | 0.5 | 6.7 |
| Acetic Acid (9.9) | Glutaric Anhydride (5.0) | 100 | 0.25 | 8.0 |
| Acetic Acid (9.9) | Glutaric Anhydride (5.0) | 100 | 0.5 | 12.6 |
| Acetic Acid (9.1) | Polyphosphoric Acid* (4.5) | 100 | 0.5 | 9.1 |
| Acetic Acid (14.9) | o-Sulfobenzoic Acid Anhydride (1) | 100 | 0.5 | 1.8 |
| Acetic Acid (7.8) | o-Sulfobenzoic Acid Anhydride (2) | 100 | 0.5 | 5.2 |
| Acetic Acid (7.8) | o-Sulfobenzoic Acid Anhydride (4.8) | 100 | 0.5 | 8.0 |
| Propanoic Acid (7.6) | Glutaric Anhydride (4.9) | 100 | 0.5 | 10.1 |

*Molarity based on c.a. 84 wt % $P_2O_5$ equivalent as anhydride equivalent, balance $H_3PO_4$.

Example 3

This example demonstrates a method of producing various anhydrides using a regenerable anhydride and an organic mono-acid under various reaction conditions in an embodiment of the invention.

The solids and/or liquids were added to 2-dram vials with polytetrafluoroethylene (PTFE) caps or 2-5 ml microwave vials with crimp caps, and each vial was equipped with a stir bar. In some trials, a corresponding co-solvent was added to the corresponding vial and sealed. The sealed vials were placed into a preheated (75-150° C.) aluminum pie block, and the reactions were stirred at 800 rpm for 1 hr. The vials were removed from the heat and cooled on a room temperature aluminum pie block. If the reaction mixture was homogeneous at room temperature, a dichloromethane (DCM) standard was added, and an NMR sample was prepared. If the reaction mixture was a solid at room temperature, an appropriate amount of DMSO or DMF was added to the reaction mixture to dissolve the solids. A DCM standard was added to the reaction mixture and an NMR sample was prepared. The solutions were added to NMR tubes containing a capillary containing $C_6D_6$ and NMRs were taken with long relaxation delays to ensure quantitative NMRs. The reaction conditions are set forth in Table 2, and the products are set forth in Table 3.

TABLE 2

| Entry | T (° C.) | Acid (HX) | Anhydride ($X_2'O$) | Co-solvent (CS) | [CS] (M) | [HX] (M) | [$X_2'O$] (M) |
|---|---|---|---|---|---|---|---|
| 1 | 75 | Acetic | Glutaric | N/A | N/A | 8.75 | 4.38 |
| 2 | 75 | Propionic | Glutaric | N/A | N/A | 8.75 | 4.38 |
| 3 | 75 | Chloroacetic | Glutaric | N/A | N/A | 7.87 | 3.94 |
| 4 | 110 | Acetic | Glutaric | N/A | N/A | 8.75 | 4.38 |
| 5 | 110 | Propionic | Glutaric | N/A | N/A | 8.75 | 4.38 |
| 6 | 110 | Chloroacetic | Glutaric | N/A | N/A | 7.87 | 3.94 |
| 7 | 110 | Benzoic | Glutaric | N/A | N/A | 6.30 | 3.15 |
| 8 | 110 | Cinnamic | Glutaric | N/A | N/A | 5.25 | 2.63 |
| 9 | 150 | Acetic | Glutaric | N/A | N/A | 8.75 | 4.38 |
| 10 | 150 | Propionic | Glutaric | N/A | N/A | 8.75 | 4.38 |
| 11 | 150 | Chloroacetic | Glutaric | N/A | N/A | 7.87 | 3.94 |

TABLE 2-continued

| Entry | T (° C.) | Acid (HX) | Anhydride (X₂'O) | Co-solvent (CS) | [CS] (M) | [HX] (M) | [X₂'O] (M) |
|---|---|---|---|---|---|---|---|
| 12 | 150 | Benzoic | Glutaric | N/A | N/A | 6.30 | 3.15 |
| 13 | 150 | Cinnamic | Glutaric | N/A | N/A | 5.25 | 2.63 |
| 14 | 110 | Acetic | Succinic | N/A | N/A | 8.75 | 4.38 |
| 15 | 150 | Acetic | Succinic | N/A | N/A | 8.75 | 4.38 |
| 16 | 150 | Acetic | Pyromellitic | N/A | N/A | 8.75 | 2.19 |
| 17 | 150 | Acetic | Glutaric | Cyclohexanone | 4.82 | 4.38 | 2.19 |
| 18 | 150 | Acetic | Glutaric | Cyclohexanone | 6.43 | 2.92 | 1.46 |
| 19 | 150 | Acetic | Glutaric | Cyclohexanone | 7.72 | 1.75 | 0.88 |
| 20 | 150 | Acetic | Glutaric | m-xylene | 4.09 | 4.38 | 2.19 |
| 21 | 150 | Acetic | Glutaric | m-xylene | 5.45 | 2.92 | 1.46 |
| 22 | 150 | Acetic | Glutaric | m-xylene | 6.54 | 1.75 | 0.88 |
| 23 | 150 | Myristic | Glutaric | DMF | 6.46 | 2.13 | 1.06 |
| 24 | 150 | Benzoic | Glutaric | DMF | 6.46 | 3.15 | 1.58 |
| 25 | 150 | Cinnamic | Glutaric | DMF | 6.46 | 3.15 | 1.58 |
| 26 | 75 | Acetic | Sulfobenzoic | N/A | N/A | 8.75 | 4.38 |
| 27 | 110 | Acetic | Sulfobenzoic | N/A | N/A | 8.75 | 4.38 |
| 28 | 150 | Acetic | Sulfobenzoic | N/A | N/A | 8.75 | 4.38 |
| 29 | 110 | Myristic | Glutaric | N/A | N/A | 4.25 | 2.13 |
| 30 | 110 | Trifluoroacetic | Glutaric | N/A | N/A | 10.00 | 5.00 |
| 31 | 110 | Methanesulfonic | Glutaric | N/A | N/A | 9.63 | 4.81 |
| 32 | 110 | Acetic | Propane phosphonic | N/A | N/A | 8.75 | 1.46 |
| 33 | 75 | Trifluoroacetic | Glutaric | N/A | N/A | 10.00 | 5.00 |
| 34 | 75 | Methanesulfonic | Glutaric | N/A | N/A | 9.63 | 4.81 |
| 35 | 75 | Acetic | Propane phosphonic | N/A | N/A | 8.75 | 1.46 |
| 36 | 110 | Trifluoroacetic | Glutaric | N/A | N/A | 5.00 | 5.00 |
| 37 | 110 | Trifluoroacetic | Glutaric | N/A | N/A | 10.00 | 2.50 |
| 38 | 110 | Methanesulfonic | Glutaric | N/A | N/A | 6.02 | 6.02 |
| 39 | 110 | Methanesulfonic | Glutaric | N/A | N/A | 11.00 | 2.75 |
| 40 | 110 | Acetic | Poly phosphoric | N/A | N/A | 13.11 | 2.19 |
| 41 | 110 | Acetic | Poly phosphoric | N/A | N/A | 13.99 | 1.75 |
| 42 | 75 | Trifluoroacetic | Glutaric | N/A | N/A | 10.00 | 5.00 |
| 43 | 75 | Methanesulfonic | Glutaric | N/A | N/A | 9.63 | 4.81 |
| 44 | 75 | Acetic | Poly phosphoric | N/A | N/A | 13.13 | 2.19 |
| 45 | 75 | Acetic | Propane phosphonic | N/A | N/A | 13.13 | 0.73 |
| 46 | 75 | Myristic | Glutaric | N/A | N/A | 4.25 | 2.13 |
| 47 | 150 | Trifluoroacetic | Glutaric | N/A | N/A | 10.00 | 5.00 |
| 48 | 150 | Methanesulfonic | Glutaric | N/A | N/A | 9.63 | 4.81 |
| 49 | 150 | Acetic | Poly phosphoric | N/A | N/A | 13.13 | 2.19 |
| 50 | 150 | Myristic | Glutaric | N/A | N/A | 4.25 | 2.13 |
| 51 | 150 | Acetic | Glutaric | toluene | 4.09 | 4.38 | 2.19 |
| 52 | 150 | Acetic | Glutaric | toluene | 5.45 | 2.92 | 1.46 |
| 53 | 150 | Acetic | Glutaric | toluene | 6.54 | 1.75 | 0.88 |
| 54 | 150 | Myristic | Glutaric | toluene | 4.09 | 2.13 | 1.06 |
| 55 | 150 | Myristic | Glutaric | toluene | 5.45 | 1.42 | 0.71 |
| 56 | 150 | Benzoic | Glutaric | toluene | 4.09 | 3.15 | 1.58 |
| 57 | 150 | Benzoic | Glutaric | toluene | 5.45 | 2.10 | 1.05 |
| 58 | 150 | Benzoic | Glutaric | toluene | 6.54 | 1.26 | 0.63 |
| 59 | 150 | Myristic | Glutaric | Cyclohexanone | 4.82 | 2.13 | 1.06 |
| 60 | 150 | Myristic | Glutaric | Cyclohexanone | 6.43 | 1.42 | 0.71 |
| 61 | 150 | Benzoic | Glutaric | Cyclohexanone | 4.82 | 3.15 | 1.58 |
| 62 | 150 | Benzoic | Glutaric | Cyclohexanone | 6.43 | 2.10 | 1.05 |
| 63 | 150 | Benzoic | Glutaric | Cyclohexanone | 7.72 | 1.26 | 0.63 |

TABLE 3

| Entry | Anhydride of the Acid [X₂O] (M) | Acid of the Anhydride [HX'] (M) | Acid (HX) Conversion (mol %) | Anhydride (X₂'O) Conversion (mol %) |
|---|---|---|---|---|
| 1 | 0.11 | 0.31 | 2.6% | 7.0% |
| 2 | 0.18 | 0.38 | 4.0% | 8.7% |
| 3 | 0.01 | 0.37 | 0.2% | 9.3% |
| 4 | 0.26 | 0.39 | 5.9% | 9.0% |
| 5 | 0.37 | 0.56 | 8.6% | 12.7% |
| 6 | 0.02 | 0.38 | 0.5% | 9.7% |
| 7 | 0.13 | 0.40 | 4.2% | 12.6% |
| 8 | 0.03 | 0.31 | 1.0% | 11.6% |
| 9 | 0.44 | 0.73 | 10.0% | 16.7% |
| 10 | 0.36 | 0.54 | 8.3% | 12.3% |
| 11 | 0.02 | 0.41 | 0.6% | 10.4% |
| 12 | 0.12 | 0.49 | 3.9% | 15.7% |
| 13 | 0.09 | 0.35 | 3.2% | 13.4% |
| 14 | 0.04 | N/D | 0.9% | N/D |

TABLE 3-continued

| Entry | Anhydride of the Acid [X₂O] (M) | Acid of the Anhydride [HX'] (M) | Acid (HX) Conversion (mol %) | Anhydride (X₂'O) Conversion (mol %) |
|---|---|---|---|---|
| 15 | 0.07 | N/D | 1.6% | N/D |
| 16 | 0.02 | 0.10 | 0.2% | 4.7% |
| 17 | 0.08 | 0.20 | 3.6% | 9.0% |
| 18 | 0.04 | 0.15 | 3.0% | 10.0% |
| 19 | 0.01 | 0.10 | 1.7% | 11.1% |
| 20 | 0.17 | 0.37 | 7.8% | 16.7% |
| 21 | 0.10 | 0.25 | 6.9% | 16.8% |
| 22 | 0.05 | 0.17 | 5.8% | 19.5% |
| 23 | 0.06 | 0.07 | 5.8% | 11.9% |
| 24 | 0.03 | 0.18 | 2.0% | 11.6% |
| 25 | 0.01 | 0.14 | 0.7% | 9.0% |
| 26 | 1.37 | 2.21 | 31.3% | 50.5% |
| 27 | 1.58 | 2.68 | 36.2% | 61.2% |
| 28 | 1.65 | 2.88 | 37.7% | 65.9% |
| 29 | 0.15 | 0.30 | 7.2% | 14.3% |
| 30 | 0.03 | 0.29 | 0.5% | 5.8% |
| 31 | 0.02 | 0.66 | 0.3% | 13.6% |
| 32 | 0.52 | N/D | 11.9% | N/D |
| 33 | 0.03 | 0.31 | 0.5% | 6.2% |
| 34 | 0.03 | 0.68 | 0.5% | 14.2% |
| 35 | 0.55 | N/D | 12.5% | N/D |
| 36 | 0.02 | 0.27 | 0.6% | 5.4% |
| 37 | 0.03 | 0.18 | 0.5% | 7.3% |
| 38 | 0.01 | 0.58 | 0.5% | 9.7% |
| 39 | 0.03 | N/D | 0.5% | N/D |
| 40 | 0.23 | N/D | 3.5% | N/D |
| 41 | 0.21 | N/D | 1.5% | N/D |
| 42 | 0.03 | 0.35 | 0.6% | 6.9% |
| 43 | 0.02 | 0.69 | 0.3% | 14.4% |
| 44 | 0.19 | N/D | 2.8% | N/D |
| 45 | 0.39 | N/D | 3.0% | N/D |
| 46 | 0.06 | 0.15 | 1.5% | 7.0% |
| 47 | 0.03 | 0.29 | 0.5% | 5.8% |
| 48 | 0.02 | 0.66 | 0.3% | 13.6% |
| 49 | 0.25 | N/D | 3.8% | N/D |
| 50 | 0.17 | 0.24 | 4.0% | 11.1% |
| 51 | 0.16 | 0.39 | 7.4% | 17.9% |
| 52 | 0.10 | 0.25 | 7.2% | 17.1% |
| 53 | 0.05 | N/D | 5.1% | N/D |
| 54 | 0.13 | 0.22 | 12.4% | 20.7% |
| 55 | 0.05 | 0.09 | 3.8% | 12.5% |
| 56 | 0.14 | 0.22 | 4.3% | 13.8% |
| 57 | 0.04 | 0.15 | 3.4% | 14.5% |
| 58 | 0.02 | 0.09 | 2.8% | 13.5% |
| 59 | 0.08 | 0.20 | 7.1% | 19.3% |
| 60 | 0.05 | 0.15 | 3.5% | 21.0% |
| 61 | 0.06 | 0.27 | 2.0% | 17.2% |
| 62 | 0.04 | 0.21 | 3.4% | 20.3% |
| 63 | 0.01 | 0.16 | 1.5% | 25.2% |

N/D: not determined

Example 4

This example demonstrates adding the organic mono-acid to the regenerable anhydride in stages in an embodiment of the invention.

To test the potential for multistage reactions, glutaric anhydride (10 g) was heated in a 50-ml round-bottom flask to 100° C. Acetic acid (5.25 g) was added, and the flask was sealed. After 1 hr, vacuum (10 torr (0.013 atm)) was applied for 15 min to most of the acetic acid and acetic anhydride, the system was repressurized to atmospheric pressure, and acetic acid was added again for another cycle. The results of the cycling experiment are shown in Table 4 and demonstrate that changing the local concentrations of the material (e.g., in a reactive distillation) results in higher yields than the equilibrium would allow in a single-stage batch process.

TABLE 4

| Cycle | Glutaric Anhydride Conversion (mol %) |
|---|---|
| 1 | 5.8 |
| 2 | 10.1 |
| 3 | 14.0 |
| 4 | 17.2 |
| 5 | 20.0 |
| 6 | 23.1 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of producing an anhydride of a carboxylic acid comprising:
    contacting a carboxylic acid and a thermally regenerable carboxylic acid anhydride to produce the anhydride of the carboxylic acid and a diacid of the regenerable carboxylic acid anhydride or a partially hydrolyzed regenerable carboxylic acid anhydride; wherein a reaction between the carboxylic acid and the thermally regenerable carboxylic acid anhydride excludes the use of perchloric acid;

forming a first stream comprising the anhydride of the carboxylic acid and unreacted carboxylic acid and a second stream comprising the diacid of the regenerable carboxylic acid anhydride or partially hydrolyzed regenerable carboxylic acid anhydride and unreacted regenerable carboxylic acid anhydride;

separating the unreacted carboxylic acid from the anhydride of the carboxylic acid by distillation; and recycling the separated, unreacted carboxylic acid.

2. A method of producing an anhydride of a carboxylic acid comprising:

contacting a carboxylic acid and a thermally regenerable carboxylic acid anhydride to produce the anhydride of the carboxylic acid and a diacid of the regenerable carboxylic acid anhydride or a partially hydrolyzed regenerable carboxylic acid anhydride; wherein a reaction between the carboxylic acid and the thermally regenerable carboxylic acid anhydride excludes the use of perchloric acid;

forming a first stream comprising the anhydride of the carboxylic acid and unreacted carboxylic acid and a second stream comprising the diacid of the regenerable carboxylic acid anhydride or partially hydrolyzed regenerable carboxylic acid anhydride and unreacted regenerable carboxylic acid anhydride;

separating the unreacted carboxylic acid from the anhydride of the carboxylic acid by distillation; and heating the second stream to regenerate the regenerable carboxylic acid anhydride.

3. The method of claim 2, wherein azeotropic distillation is used to regenerate the regenerable carboxylic acid anhydride.

4. The method of claim 2, wherein the regenerable carboxylic acid anhydride is recycled.

5. The method of claim 1, wherein the regenerable carboxylic acid anhydride is cyclic or can form a cyclic structure.

6. The method of claim 1, wherein the regenerable carboxylic acid anhydride has a cyclic structure of the formula $R^1$—C(O)—O—C(O)—$R^2$, in which $R^1$ and $R^2$ are linked together to form an alkylene with 1 or 2 optional double bonds, arylene, or a mixed alkylene/arylene group.

7. The method of claim 1, wherein the carboxylic acid is a $C_{1-18}$ monocarboxylic acid.

8. The method of claim 7, wherein the $C_{1-18}$ monocarboxylic acid is selected from formic acid, acetic acid, propionic acid, butanoic acid, isobutyric acid, pentanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, and a combination thereof.

9. The method of claim 1, wherein the carboxylic acid is acetic acid.

10. The method of claim 1, wherein the anhydride of the monocarboxylic acid is acetic anhydride.

11. The method of claim 1, wherein the carboxylic acid is added in excess of the regenerable carboxylic acid anhydride.

12. A method of producing an anhydride of a carboxylic acid comprising:

contacting a carboxylic acid and a thermally regenerable carboxylic acid anhydride to produce the anhydride of the carboxylic acid and a diacid of the regenerable carboxylic acid anhydride or a partially hydrolyzed regenerable carboxylic acid anhydride; wherein a reaction between the carboxylic acid and the thermally regenerable carboxylic acid anhydride excludes the use of perchloric acid; and adding the carboxylic acid over multiple stages.

13. A method of producing an anhydride of a carboxylic acid comprising:

contacting a carboxylic acid and a thermally regenerable carboxylic acid anhydride to produce the anhydride of the carboxylic acid and a diacid of the regenerable carboxylic acid anhydride or a partially hydrolyzed regenerable carboxylic acid anhydride; wherein a reaction between the carboxylic acid and the thermally regenerable carboxylic acid anhydride excludes the use of perchloric acid; and adding a salt of the carboxylic acid.

14. A method of producing an anhydride of a carboxylic acid comprising:

contacting a carboxylic acid and a thermally regenerable carboxylic acid anhydride to produce the anhydride of the carboxylic acid and a diacid of the regenerable carboxylic acid anhydride or a partially hydrolyzed regenerable carboxylic acid anhydride; wherein a reaction between the carboxylic acid and the thermally regenerable carboxylic acid anhydride excludes the use of perchloric acid;

forming a first stream comprising the anhydride of the carboxylic acid and unreacted carboxylic acid and a second stream comprising the diacid of the regenerable carboxylic acid anhydride or partially hydrolyzed regenerable carboxylic acid anhydride and unreacted regenerable carboxylic acid anhydride;

separating the unreacted carboxylic acid from the anhydride of the carboxylic acid by distillation; and diverting a portion of the carboxylic acid to a vessel containing the second stream.

15. The method of claim 2, wherein the regenerable carboxylic acid anhydride is cyclic or can form a cyclic structure.

16. The method of claim 2, wherein the regenerable carboxylic acid anhydride has a cyclic structure of the formula $R^1$—C(O)—O—C(O)—$R^2$, in which $R^1$ and $R^2$ are linked together to form an alkylene with 1 or 2 optional double bonds, arylene, or a mixed alkylene/arylene group.

17. The method of claim 2, wherein the carboxylic acid is a $C_{1-18}$ monocarboxylic acid.

18. The method of claim 17, wherein the $C_{1-18}$ monocarboxylic acid is selected from formic acid, acetic acid, propionic acid, butanoic acid, isobutyric acid, pentanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, and a combination thereof.

19. The method of claim 2, wherein the carboxylic acid is acetic acid.

20. The method of claim 2, wherein the anhydride of the monocarboxylic acid is acetic anhydride.

21. The method of claim 2, wherein the carboxylic acid is added in excess of the regenerable carboxylic acid anhydride.

* * * * *